(12) United States Patent
Guay (10) Patent No.: US 8,308,388 B2
(45) Date of Patent: Nov. 13, 2012

(54) FLUID DELIVERY SYSTEM

(75) Inventor: Gordon Gerald Guay, Chelmsford, MA (US)

(73) Assignee: The Gillette Company, Boston, MA (US)

( * ) Notice: Subject to any disclaimer, the term of this patent is extended or adjusted under 35 U.S.C. 154(b) by 857 days.

(21) Appl. No.: 12/350,286

(22) Filed: Jan. 8, 2009

(65) Prior Publication Data

US 2009/0180826 A1    Jul. 16, 2009

Related U.S. Application Data

(60) Provisional application No. 61/010,895, filed on Jan. 11, 2008.

(51) Int. Cl.
*B43K 5/00* (2006.01)
*B43K 8/06* (2006.01)

(52) U.S. Cl. ........................................ 401/198

(58) Field of Classification Search ............ 401/34, 401/35, 198, 196
See application file for complete search history.

(56) References Cited

U.S. PATENT DOCUMENTS

| | | | | |
|---|---|---|---|---|
| 2,726,416 A * | 12/1955 | Lepkowski | ............ | 401/143 |
| 3,133,309 A | 5/1964 | Dewayne | | |
| 4,017,871 A * | 4/1977 | Hubbard | ............ | 346/140.1 |
| 5,306,092 A * | 4/1994 | Jenq | ............ | 401/47 |
| 5,899,619 A * | 5/1999 | O'Shei | ............ | 401/35 |
| 5,937,874 A | 8/1999 | Guay et al. | | |
| 6,883,995 B1 * | 4/2005 | Gueret | ............ | 401/202 |
| 6,994,932 B2 | 2/2006 | Kinkelaar et al. | | |
| 2007/0110506 A1 | 5/2007 | Erickson et al. | | |
| 2007/0286669 A1 | 12/2007 | Nuebel et al. | | |
| 2008/0149126 A1 * | 6/2008 | Abergel | ............ | 132/200 |

OTHER PUBLICATIONS

PCT International Search Report with Written Opinion in corresponding Int'l appln.
PCT/IB2009/050076 dated Jan. 19, 2010.

* cited by examiner

*Primary Examiner* — Huyen Le
(74) *Attorney, Agent, or Firm* — Ronald T. Sia; Kevin C. Johnson; Steven W. Miller (57) ABSTRACT

A fluid delivery system includes an applicator having gradient foam where the gradient foam includes a fluid and the applicator has an applicator surface area open to the environment such that the fluid is passively dispensed onto a surface independent of gravity through the applicator surface area. The gradient foam may be encompassed by a holder. A fluid reservoir in the applicator holder is used to replenish fluid. A cap covers the gradient foam to prevent the foam drying out. The types of surfaces that the fluid delivery system may be applied to can be hard or soft, such as wood or skin and hence, the fluid delivery system may be used for many applications in the home, health/medicine, beauty, feminine, baby, personal, fabric, pet and food areas.

36 Claims, 5 Drawing Sheets

PRIOR ART

FLUID DELIVERY SYSTEM

CROSS REFERENCE TO RELATED APPLICATION

This application claims the benefit of U.S. Provisional Application No. 61/010,895 filed Jan. 11, 2008.

FIELD OF THE INVENTION

The field of the invention is fluid delivery systems and more particularly, passive, gravity independent delivery devices enabling consistent and tailorable delivery of fluid formulations.

BACKGROUND OF THE INVENTION

There are a variety of methods that exist today to deliver fluids. Within those, there are three broad prior art categories of fluid delivery types. One prior art category would include mechanical systems, such as brushes, pads, and foams. A second category would include pressurized or electromagnetic driven systems which are generally active. A third category would include capillary (or wick) based systems which are generally passive.

Within the first mechanical systems category, where the system holds and releases fluids by mechanical means via brushes, pads and/or foams, the prior art typically includes products such as paint brushes, foam applicators for cosmetics, and other brush-based fluid delivery systems.

A drawback of using fluid delivery systems within this category is that generally, there is lack of consistency in fluid output and they require continuous refill.

One common class within the second pressurized delivery category is a pump-based system which may typically include a peristaltic pump and/or other electrical, mechanical, electromagnetic or pressure driven devices to deliver a specific or defined level of fluid or fluid. A well-known product founded on pump-based principles would be a paint system that continuously dispenses paint into a roller such as the commercially available Wagner paint sprayer device. Other examples include squirt gun type tank sprayers used in fertilizer or bug spraying.

A drawback of this type of pump-based delivery system is that it is active and hence, requires energy to operate, thereby making it a relatively costly solution for a desired low cost or mass marketed product.

Another drawback of fluid delivery with a pump is that the system is either always on or would require actuation, thus, while the system may provide greater versatility it may not deliver the specific dose for a desired application, a critical factor to functionality or product aesthetics.

The third category of fluid delivery includes capillary based systems. Prior art capillary systems would include sintered powders, filamentous, foam or fiber based systems.

Some common examples of capillary system products would be wick-based air freshener fragrance-delivery products or some ink jet printer delivery products. The fiber based systems use bundles or other structures that are physically attached to each other. Some examples of these are: felt tip pens, magic markers, porous dome applicators (e.g. sintered pressed powder). However, as with other prior art solutions, fiber bundles are not necessarily consistent in the amount of product delivered and attempts to solve that problem by varying the applicator size adds difficulty. Furthermore, multiple uses of these systems can result in cloggage over time rendering inconsistent delivery of material to the desired dose.

The gradient or compressed foam described for fuel cells in U.S. Pat. No. 6,994,932 requires both a pump and capillary-based system, increasing the cost and complexity of the final device. Additionally, a limitation of the system described therein is that in its application to fuel cells for electronic devices it is a self-contained system, i.e. not open to the environment due to volatility of the fuel fluid.

Although these prior art systems described above function properly, some have inconsistent fluid delivery, some require energy, some are closed to the environment and there can be great variability in fluid delivery due to manufacturing, inconsistencies from product to product, and/or changes within a given product over time.

Further, many prior art systems are limited as they do not provide a continuous, tailored and precise fluid delivery system nor the capability of using a varying number and type of fluids, such as aqueous water or non-aqueous or oil based fluids.

A need exists to deliver fluids passively, independently of orientation and gravity, open to the environment and with the ability to tailor the amount of fluid delivered to a unit of area, thereby reducing cost and increasing effectiveness.

A further need exists to deliver any types of fluid, or a plurality of fluids or formulations directly to any type of surface (i.e. hard, soft, fabric, skin, hair, teeth) thereby covering many application areas.

SUMMARY OF THE INVENTION

In one aspect, the invention features, in general, a fluid delivery system including at least one gradient foam, each having an applicator surface area open to the environment, wherein the gradient foam is filled with a fluid which is passively and consistently dispensed independent of gravity when said applicator surface area contacts a surface. The fluid delivery system includes a holder encompassing the gradient foam. In a further aspect of the invention the holder includes at least one fluid reservoir and is made of an of an injected plastic polymer material. In another aspect of the invention, a cap covers each applicator surface area. In another aspect of the invention, each gradient foam has a varying compression in the range of about zero (0) to about twenty (20) over a length of the gradient foam, and is made of polyurethane, melamine, cellulosic, PVC, polystyrene, polyethylene, or polyester materials. In a still further embodiment of the invention, each gradient foam is formed by a composite of a plurality of foams having different compression ratios. In a particular embodiment, the fluid is a liquid having at least one ingredient with the fluid having a viscosity in the range of about 0.1 to about 2000 centipoise.

Particular embodiments of the invention include one or more of the following features or advantages. In another embodiment the applicator surface area has a domed shape. In yet another embodiment, the gradient foam may be chemically modified.

In a still further embodiment, there is a first fluid within a first gradient foam and a second fluid within a second gradient foam wherein the first and second fluids are of a different type and the first and second gradient foams have the same compression ratios. In a yet still further embodiment, there is a first fluid within a first gradient foam and a second fluid within a second gradient foam wherein the first and second fluids are of a different type and the first and second gradient foams have different compression ratios. Preferably, the first and second fluids are applied onto the surface from first and second applicator surface areas, respectively. The first and second fluids can interact to form a third component that is applied onto the surface. A first fluid can be deposited onto one side of the surface from a first applicator surface area and a second fluid can be deposited onto another side of the surface from a second applicator surface area. In addition, as the applicator surface area increases, the amount of fluid dispensed onto the surface increases in a directly proportional manner.

The surface can be made of wood, ceramic, plastic, glass, metal, skin, hair, nails, fur, fabric, oral structures or cavities (e.g. teeth). The fluid can be used in application areas comprising home, health/medicine, beauty, feminine, baby, personal, fabric, pet, and food.

In another aspect, the invention features, in general, a method of delivering fluid including filling at least one gradient foam with a fluid, each gradient foam having at least one applicator surface area open to the environment, and contacting a surface with the applicator surface area wherein the fluid is passively and consistently dispensed onto said surface independent of gravity through the applicator surface area. Each of the gradient foams can be encompassed by a holder.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

For purposes of the present invention, the term "fluid" will be defined as a substance such as a liquid that is capable of flowing and that changes its shape at a steady rate when acted upon by a force tending to change its shape and may be used interchangeably or signify the following terms: liquid, water, alcohol, silicone, oil, emulsion or any combination of these fluid terms or with any additional soluble components.

Fluids desired in the present invention are of a type that produce low viscosity formulations with the capability of flowing within a given pore structure where viscosity is low enough to function via capillary action and does not require any pressure for delivery.

Additionally, the term "wicking" and "capillary action" are deemed equivalent for purposes of the present invention and used interchangeably.

Figure 1:
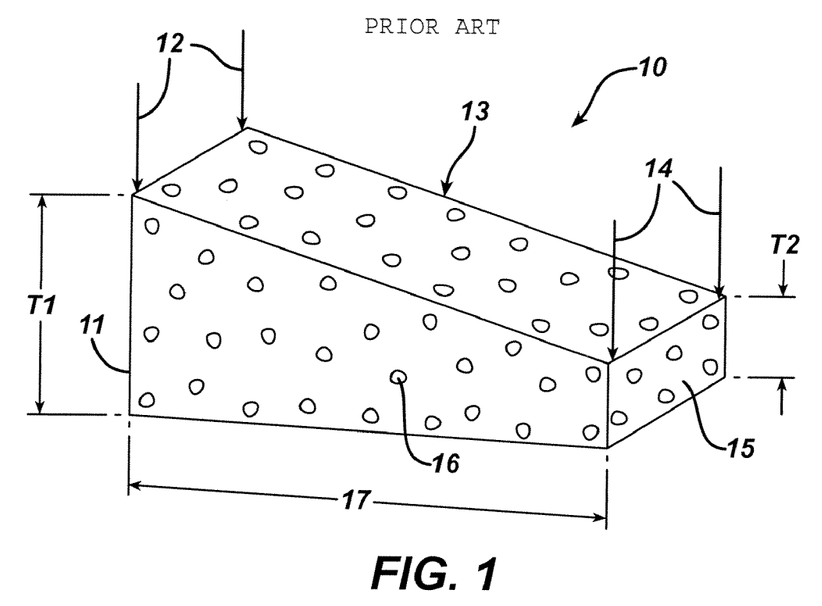
FIG. 1 is a schematic diagram of a prior art wedge of wicking material prior to felting.

Referring now to FIG. 1 shows a prior art wedge of foam or wicking material prior to felting. Wicking is generally known to mean the drawing off of a fluid by capillary action. As described in "Fluid Fuel Reservoir for Fuel Cells", U.S. Pat. No. 6,994,932, the wicking structure therein is made with a foam with a capillary gradient, such that the flow of fluid fuel is directed from one region of the structure to another region as a result of the differential in capillarity between the two regions, where the direction of capillarity flow of fluid is from a lower capillarity region to a higher capillarity region, or otherwise stated from low to high density regions of the foam.

Figure 4:
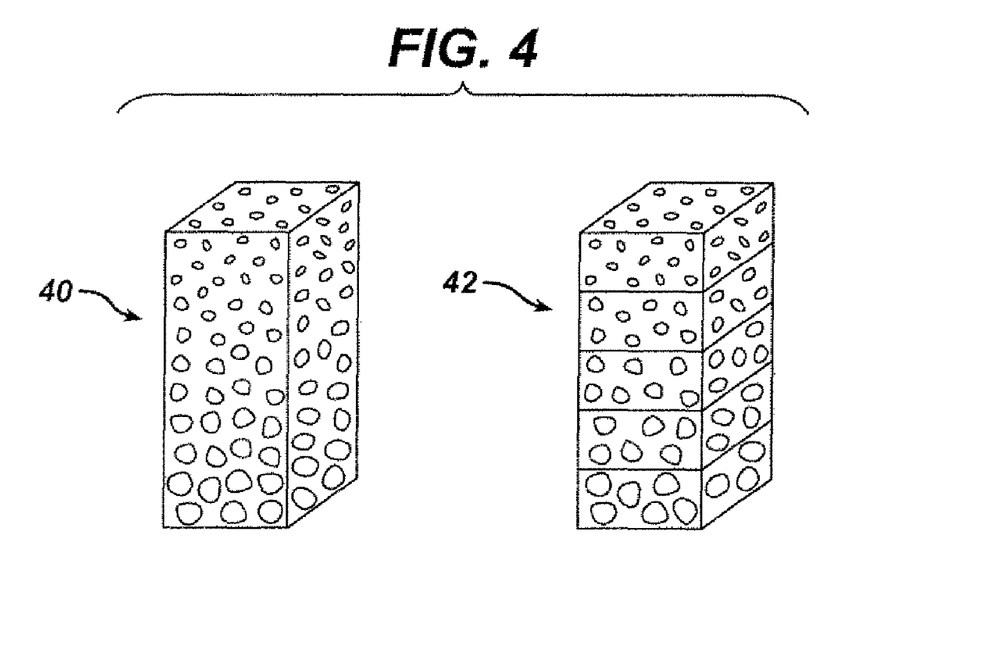
FIG. 4 is a diagram of gradient foam structures in accordance with the present invention.

In the prior art, one method for producing a material with a capillary gradient is to "felt," or compress, or heat set, foam to varying degrees of compression or pore size along its length. Another method for producing a material with a capillary gradient is to assemble a composite of individual components with distinctly different capillarities that are physically attached to each other, the latter as will be discussed in conjunction with FIG. 4.

A piece of foam or wicking material is generally known to have many pores, generally of consistent size, typically described as having a certain number of pores per square inch (ppi). PPI designations are generally used for foams. It follows that the more pores (per unit area) that exist in the foam, the smaller the pores are, thereby rendering the foam less porous. Hence, the fewer pores there are in the foam, the bigger the pore size, thereby rendering the foam more porous. The pore sizes in a piece of foam with consistent pore size can be made to vary as will be described below with respect to FIGS. 1 and 2. By varying the pore size in a piece of foam (also referred to as changing the gradient of porosity or having a capillary gradient), one side of the foam will be more porous than the other. Therefore, any fluid placed in the foam will trend from the more porous area (largest pores) toward the least porous area (smallest compressed pores).

When open cell foams are manufactured they have "windows" of a thin layer of material within the general foam structure. These windows are typically removed either chemically or via a zapping process with a flash flame to produce an open cell structure described as reticulated foam. It is desirable to produce gradient foams using foam that has been reticulated.

Figure 2:
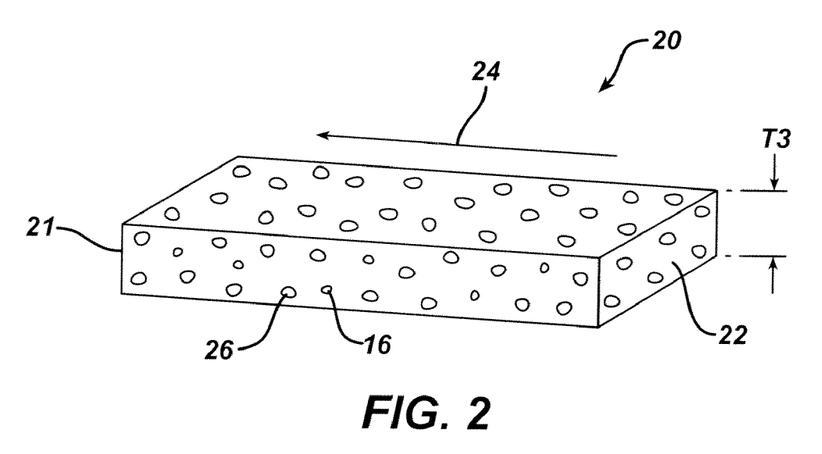
FIG. 2 is a schematic diagram of the wedge of wicking material of FIG. 1 after felting.

FIGS. 1 and 2 illustrate the before and after schematics of a wicking material, such as foam, with a capillary gradient.

As shown in FIG. 1, a wedge-shaped piece 10 of foam of consistent density and consistent pore size has a first thickness T1 at a first end 11 and a second thickness T2 at a second end 15. The foam 10 has a predefined starting material and porosity and is physically cut at an angle to form the wedge-shape as shown in FIG. 1. Foam piece 10 has evenly spaced pores 16 and consistent pore size, with initial pore size of each pore 16 preferably ranging from about 20 pores per square inch (ppi) to about 120 ppi. The angle of gradient varies with the thicknesses T1 and T2, and the length of foam piece 17.

Foam piece 10 is preferably made of polyurethane but can be made from, though not limited to, any of the following materials: melamine, cellulosic, PVC, polystyrene, polyethylene, and polyester. The material of the foam piece can vary and can also be surface treated to achieve other surface energy properties. For instance, the foam piece 10 can be surface treated with a chemical to increase hydrophobicity (i.e. having no affinity for water) or the starting foam material can be hydrophobic in nature.

To produce a material with varying pore sizes or a capillary gradient, one may subject the foam to varying degrees of compression along its length. Another way is to assemble together several different pieces of reticulated foam having different pore sizes with different capillarities or compression ratios to create a composite material.

To accomplish the compression, the piece of foam 10 is subjected to a felting step which involves high temperature compression for a desired time thereby compressing the foam piece 10 to a consistent thickness T3, which is preferably a thickness less than or equal to T2 and less than the thickness T1 as depicted in FIG. 2. The foam produced from foam piece 10 after this type of compression is depicted in FIG. 2 and is herein referred to as gradient foam 20.

It should be noted that a greater compressive force, represented by arrows 12 in FIG. 1, is required to compress the material from T1 to T3 at the first end 11 than is the compressive force, represented by arrows 14 in FIG. 1 required to compress the material from T2 to T3 at the second end 15.

When the foam 10 is compressed, the pore sizes in foam 20 are also compressed as depicted in FIG. 2, because the construction or structure around the pores 16, i.e. the voids 26, has been destroyed. This results because the compression causes the collapse of the structures around the pores and in many instances the "compressed pores" may not look as they did in their pre-compression state, but they are not necessarily smaller. This visual effect is a product of the smaller voids because the greater the compression, the smaller the voids over the length of the foam. It should be noted that some pores may remain intact after compression. For purposes of description herein the term "compressed pores" is generally meant to signify both the pores 16 and the voids 26 that are produced in FIG. 2.

The compression ratio (T1/T2) of the foam material preferably ranges from about zero (0) to about twenty (20) for gradient foam 20. The compression varies along the length of the felted or gradient foam 20 shown in FIG. 2, with the greatest compression having occurred at the first end 21 (T1 to T3) as compared with the second end 22 (T2 to T3).

Accordingly, after compression, the compressed pores 16 and 26 are smaller at the first end 21 than at the second end 22. The compression ratio of compressed pores 16 and 26 vary from about zero (0) at the first end 21 to about twenty (20) times at the second end 22.

The capillary action or capillarity is inversely proportional to the effective capillary radius, and the effective capillary radius decreases with increasing firmness or compression. Accordingly, the fluid will flow to the hardest (or the most compressed portion of the gradient structure) part of the gradient foam 20.

Arrow 24 in FIG. 2 represents the direction of capillary flow from the region of lower felt firmness or capillarity to higher felt firmness or capillarity. Thus, if a wicking material or wicking structure is formed with a material or composite material having a particular capillary gradient, any fluid wicked into the material may be directed to flow as shown by arrow 24, from one region of the material with lower compression ratio to another region with higher compression ratio, or from the bigger compressed pore sized end to the smaller compressed sized end. Because of the compressed pores in the gradient foam 20, this fluid flow is accomplished passively and independent of gravity.

Figure 3:
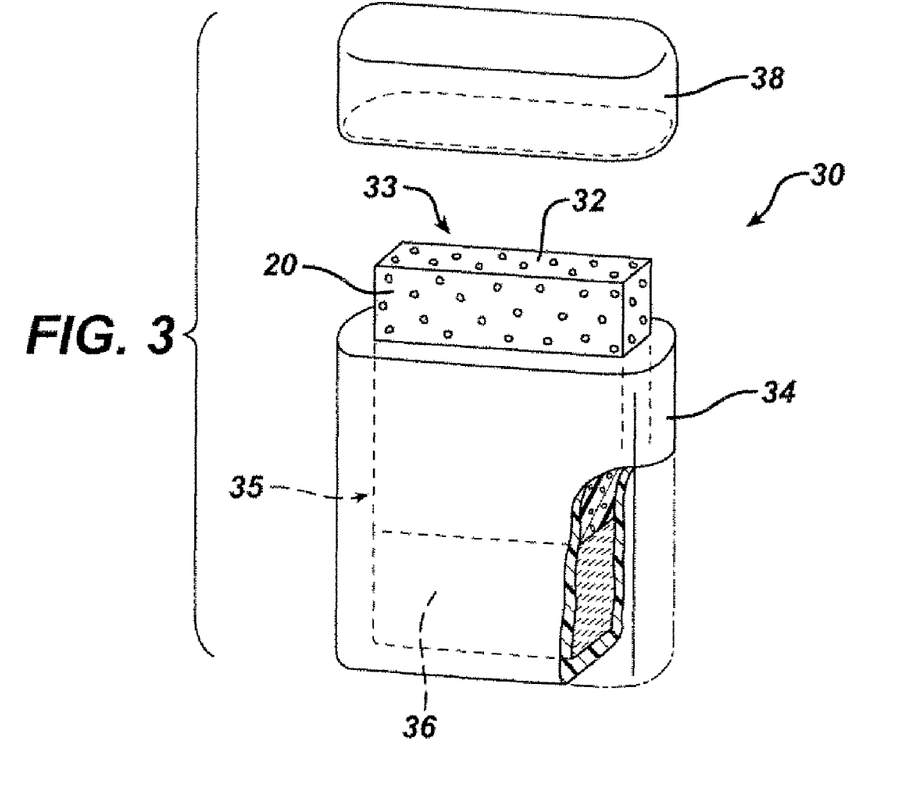
FIG. 3 is a diagram of an applicator with a holder and gradient foam in accordance with the present invention.

Referring now to FIG. 3, an applicator 30 is shown to include the gradient foam 20 of FIG. 2 having an applicator surface area 32, a first end 35 which is inserted into a holder 34 and a second end 33 which is open to the environment in accordance with a preferred embodiment of the present invention, such that regardless whether a simple fluid (e.g. with one or few ingredients) or a complex formulation is wicked into the foam 20, the fluid will consistently flow towards the applicator surface area 32 at second end 33, independent of gravity or orientation of applicator 30. The fluid will flow out of area 32 (into the environment) when in contact with another surface. Contrary to prior expectations, the fluid flows to the applicator surface area 32 with no pump, pressure or other active mechanism in accordance with a preferred aspect of the present invention.

The applicator 30 as shown in FIG. 3 has a substantially rectangular shape, but any shape, such as circular or square or any other desired, is contemplated as being within the scope of the present invention. Applicator 30 may be a stand alone unit, or part of an on-demand liquid delivery system (e.g. a product applicator). Applicator 30 may be treated as a disposable component of any type of application device. The applicator 30 may be a single use or a multiple use product; hence, the amount of fluid in the foam will vary accordingly. Since many different types of applications are envisioned for applicator 30, the dimensions of applicator 30 will vary widely depending on the intended application and the desired fluid dose per unit area.

Similarly, the applicator surface area 32 can be substantially rectangular and flat as shown in FIG. 3 or it can be changed or sculpted to any desired shape (e.g. domed), or have protruding, rounded or beveled nubs on the surface 32 or any type of different edges. Furthermore, the exposed delivery applicator surface area 32 can be changed to tailor any required fluid release. The relationship between surface area and fluid release is discussed below with regard to FIG. 8.

The holder 34, as shown in FIG. 3, except for the exposed applicator surface area 32, substantially encompasses gradient foam 20 in accordance with a preferred embodiment of the present invention. Additionally, the holder 34 can be formulated as a laminate and placed directly onto the foam 20. A small section of end 33 may extend past the holder 33 or be exposed to the environment as shown in FIG. 3.

The fluid in gradient foam 20 may empty with use or dry out or evaporate over time. This time depends on how much fluid was initially wicked into the foam 20. When the majority of the fluid in gradient foam 20 runs out or dries out, the "empty" gradient foam 20 can be removed and replaced with new foam or a new applicator having a new foam, where the foam is pre-loaded with fluid, or the "empty" gradient foam 20 can be refilled with fluid. Furthermore, applicator 30 may include one or more fluid reservoirs 36 within the holder 34 and preferably in contact or proximal to the foam 20 (e.g. underneath or behind the bottom of foam 20). The fluid reservoir 36 provides additional fluid for applicator 30 to replenish foam 20 if the fluid in gradient foam 20 runs out or dries out.

Cap 38 in the preferred embodiment of the present invention of FIG. 3, covers the applicator surface area 32 and end 33 circumventing the acceleration of the drying out of gradient foam 20 when not in use. Cap 38 may also be integrated with holder 34 (not shown). In some instances, the fluid will not dry out readily (i.e. oil-based formulation) and a cap or cover may or may not be necessary. In an alternate embodiment of the present invention, there is no cap but rather a nonvolatile formulation within the applicator or foam itself that assists in preventing fluids from drying out.

The holder 34 and cap 38 are preferably made of an injected plastic polymer material, such as polypropylene, polyethylene, ABS (acrylonitrile butadiene styrene), nylon, polycarbonate, when manufacturing via injection molded processes or foil/plastic laminates, when manufacturing within a foil package with a stand alone fluid dispenser and dependent on the type of formulation. The applicator 30 may be manufactured to include two or more pieces such as the holder 34 and foam 20 or it may be manufactured as a single piece part using a PVC (poly vinyl chloride) dip coated process.

The foam material of gradient foam 20 is preferably made of polyurethane but can be made from, though not limited to, any of the following materials: melamine, cellulosic, PVC, polystyrene, polyethylene, or polyester. Furthermore, foam 20 can be a single contiguous foam material with varying compressed pore sizes (i.e. continuous gradient of porosity) as shown in FIG. 2 and again in FIG. 4 at 40 or foam 20 can be a laminate or a composite of several foams each having different capillarities or compression ratios (as shown at 42 in FIG. 4), therefore producing a gradient of laminated foam porosities.

The gradient foam 20 can be any color, shape or have any varying size of pores desired for a specific application. Preferably, the starting range of pore size for gradient foam 20 before compression is generally from about 20 ppi to about 120 ppi.

The applicator surface area 32 can be directly applied to or directly touch any type of surface, hard or soft, in application areas such as home, health/medicine, beauty, feminine, baby, personal, fabric, pet, food, or other care areas, where such surfaces could be, though not limited to, wood, ceramic, plastic, glass, metal, skin, hair, nails, fur, fabric, oral structures or cavities (e.g. teeth). Since the fluid within foam 20 may also be a food, drink, medicant, or drug, it is contemplated that the foam 20 be biocompatible.

It is contemplated in the present invention that the fluid or fluids in the gradient foam can be of any type of substance, such as a liquid that is capable of flowing. The fluid is wicked into or fills up the gradient foam 20. The fluid can be aqueous or non-aqueous, having from at least one ingredient or components to many complex ingredients. The fluid in the gradient needs to be "flowable," that is, it should have a viscosity low enough to allow the fluid to freely move through the foam. The more viscous (e.g. gel or cream) the fluid, the less likely the fluid will move through the foam without the need of pressure to push it through the pores. Accordingly, the viscosity for fluids used in the present invention preferably ranges from about 0.1 to about 2000 centipoise. Additionally, to allow proper flow for aqueous and non-aqueous fluids, empirical determinations need to be made for specific chemistries and surface energy profiles of the foam and/or fluid. And it further may be necessary, in order to achieve proper delivery for a given fluid, to modify the foam 20 chemically or via plasma-etching.

Generally, the type of fluid formulation in the foam is dictated by the application area for applicator 30. For instance, for personal care or antiperspirant applications, the foam 20 is wicked with an antiperspirant and/or deodorant type fluid formulation. For cleaning a hard surface or fabric, the foam is wicked with a cleaning agent fluid formulation. There are many potential applications for applicator 30 or foam 20. These include cosmetic applications, oral care/ toothbrush applications, shaving systems, antiperspirants, stain removers, delivery of fluid detergents, odor absorbers, anti-tick/flea formulation delivery, hair colorants, hair bleaching agents, and fragrance delivery, just to name a few.

In an alternate embodiment of the present invention, it is contemplated that for ease of application, foam 20 may also act as a dispensing system or reservoir, allowing for precise, continuous delivery of a fluid (with any simple or complex or combination fluid).

Figure 5:
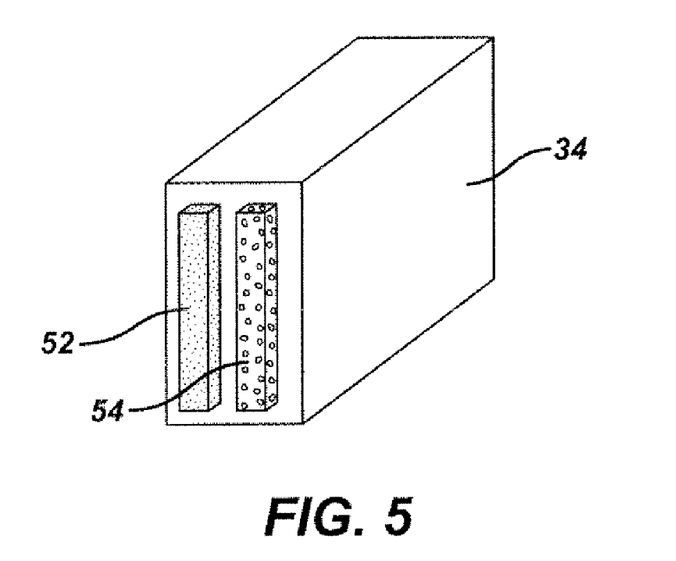
FIG. 5 is a diagram of an applicator in accordance with an alternate embodiment of the present invention.

In accordance with yet a further alternate embodiment of the present invention, the holder 34 can preferably include two or more gradient foams, with two foams shown in FIG. 5 indicated by gradient foam 52 and gradient foam 54. Foams 52 and 54 may have different gradient of porosities and may contain different fluid ingredients or formulations. For instance, foam 52 may contain a fluid ingredient or non-gradient, erodable material such as a powder or a solid while foam 54 may be a purely fluid ingredient such as a lotion, depending on the application desired. Furthermore it is contemplated that the fluids or ingredients of foam 52 may interact with the fluids or ingredients of foam 54 to form a third fluid ingredient or component to be applied onto the surface. For instance, the two fluids may be selected so that they react to form peroxide, useful for bleaching. The two fluids may be selected to deposit a film or to generate gas or heat. Some other examples of two component systems that could be applied to the novel use with foams 52 and 54 are found in U.S. Pat. No. 5,937,874, which discloses forming active agents for dental floss.

Figure 6:
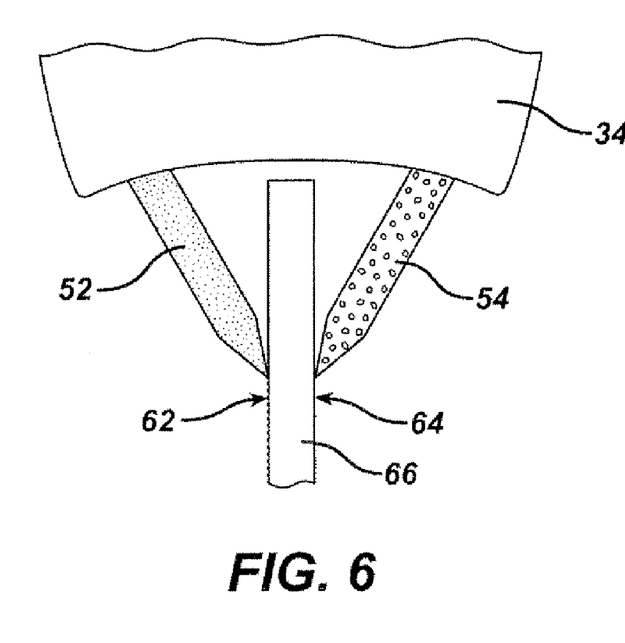
FIG. 6 is a diagram of an applicator in accordance with a yet another alternate embodiment of the present invention.

Additionally, the present invention contemplates that gradient foams 52 and 54 may be organized or oriented in any manner desired to benefit a particular application. For instance, a surface 66, such as strands of hair or a piece of fabric may be passed in between foams 52 and 54 as depicted in FIG. 6 where each foam 52 and 54, deposits a fluid (which could be the same or different) onto each side 62 and 64, respectively, of the surface 66. Hence, as the surface 66 is pulled through the applicator surfaces 62 and 64 of foam pieces 52 and 54, the ingredients from foam 52 and 54 are activated onto surface 66 immediately during use and the ingredients from foams 52 and 54 may come in contact with each other. It may alternatively be desired to serially deposit fluids rather than simultaneously, e.g. foam 52 deposits its fluid before foam 54 deposits its fluid.

Figure 7:
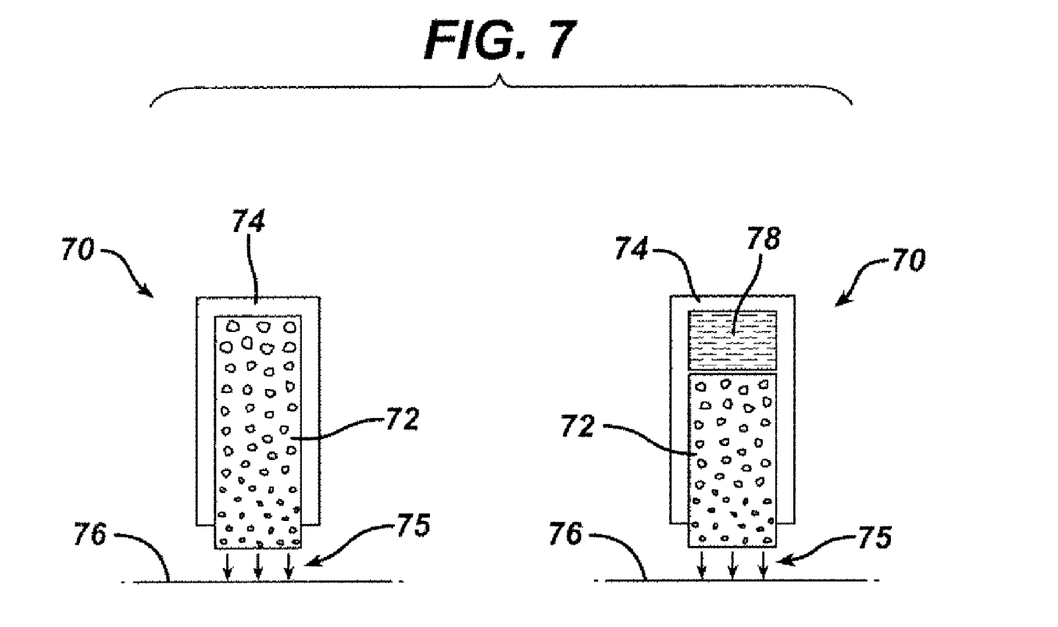
FIG. 7 shows an application for an applicator in accordance with the present invention.

FIG. 7 shows examples of applicators 70 having a gradient foam 72 encompassed by holder 74 with fluid being applied to a skin surface 76 as shown by arrows 75. Holder 74 encompasses gradient foam 72 but may also have a fluid reservoir 78 as shown in FIG. 7. The applicator 70 is depicted inverted of the diagram in FIG. 3; however, this is not indicative that gravity is necessary for optimal release of the fluid within the foam 72 to the skin 76, but rather to illustrate how a user might most commonly utilize the applicator 70.

Figure 8:
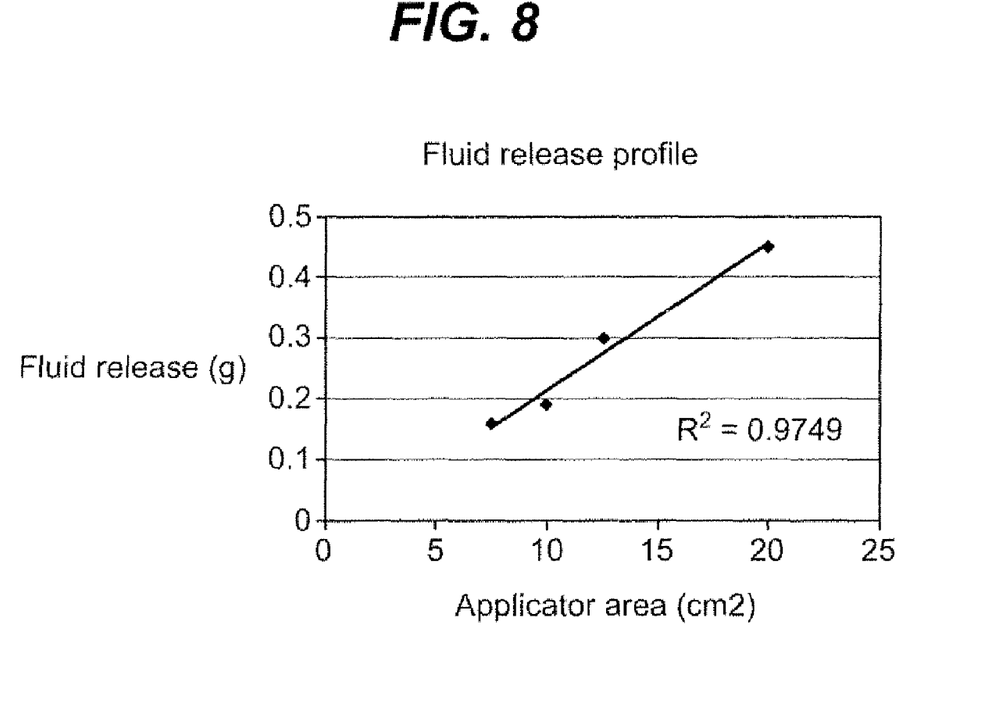
FIG. 8 is a graph depicting the relationship between the applicator surface area and average fluid released.

The overall relationship of the applicator surface area versus the average fluid released from a gradient foam such as those described above in conjunction with the preferred embodiments of the present invention is shown in the graph of FIG. 8. As depicted, there is a substantially linear relationship that results, such that, as the applicator surface area increases, the amount of fluid released increases in a directly proportional manner. It is important to note that the data depicted in the graph of FIG. 8 was determined empirically for a specific formulation and specific gradient foam, the dose delivered on a skin surface at a specific application speed (e.g. how quickly the applicator moves across the skin).

These results (i.e. for a given formulation, increasing the applicator surface area increases the dose in a linear fashion) will generally hold true regardless of the type of fluid or formulation delivered from the compressed or gradient foam. In other words, it is expected to achieve the same dose profile per unit area of applicator per formulation, speed of application and type of applicator surface.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A fluid delivery system comprising:
at least one gradient foam, each having an applicator surface area open to the environment, wherein said at least one gradient foam is filled with a fluid which is passively and consistently dispensed independent of gravity when said applicator surface area contacts a surface, wherein said at least one gradient foam has a varying compression ratio in the range of about 0 to about 20 over a length of said at least one gradient foam, and wherein the gradient foam has a continuous gradient of porosity.

2. The system of claim 1 wherein said fluid delivery system further comprises a holder encompassing said at least one gradient foam.

3. The system of claim 2 wherein said holder further comprises at least one fluid reservoir.

4. The system of claim 2 wherein said holder is made of an injected plastic polymer material.

5. The system of claim 1 further comprising a cap to cover each of said at least one applicator surface areas.

6. The system of claim 1 wherein said at least one gradient foam is comprised of polyurethane, melamine, cellulosic, PVC, polystyrene, polyethylene, or polyester materials.

7. The system of claim 1 wherein said at least one gradient foam is formed by a composite of a plurality of foams having different compression ratios.

8. The system of claim 1 wherein said fluid is a liquid having at least one ingredient.

9. The system of claim 1 wherein a viscosity of said fluid is in the range of about 0.1 to about 2000 centipoise.

10. The system of claim 1 wherein said applicator surface area has a domed shape.

11. The system of claim 1 wherein said at least one gradient foam may be chemically modified.

12. The system of claim 1 further comprising a first fluid within a first gradient foam and a second fluid within a second gradient foam wherein said first and second fluids are of a different type and said first and second gradient foams have the same compression ratios.

13. The system of claim 1 further comprising a first fluid within a first gradient foam and a second fluid within a second gradient foam wherein said first and second fluids are of a different type and said first and second gradient foams have different compression ratios.

14. The system of claim 12 or 13 wherein said first and second fluids are applied onto said surface from first and second applicator surface areas, respectively.

15. The system of claim 12 or 13 where said first and second fluids interact to form a third component that is applied onto said surface.

16. The system of claim 12 or 13 wherein said first fluid is deposited onto one side of said surface from a first applicator surface area and said second fluid is deposited onto another side of said surface from a second applicator surface area.

17. The system of claim 1 wherein as the applicator surface area increases, the amount of fluid dispensed onto said surface increases in a directly proportional manner.

18. The system of claim 1 wherein said surface comprises wood, ceramic, plastic, glass, metal, skin, hair, nails, fur, fabric, oral structures or cavities.

19. The system of claim 1 wherein said fluid can be used in application areas comprising home, health/medicine, beauty, feminine, baby, personal, fabric, pet, and food.

20. A method of delivering fluid, comprising the steps of:
filling at least one gradient foam with a fluid, each said at least one gradient foam having at least one applicator surface area open to the environment, and contacting a surface with the applicator surface area wherein said fluid is passively and consistently dispensed onto said surface independent of gravity through said applicator surface area, wherein said at least one gradient foam has a varying compression ratio in the range of about 0 to about 20 over a length of said at least one gradient foam, and wherein the gradient foam has a continuous gradient of porosity.

21. The method of claim 20 wherein said at least one gradient foam is encompassed by a holder.

22. The method of claim 20 wherein said at least one gradient foam has a compression in the range of 0 to 20 over a length of said at least one gradient foam.

23. The method of claim 20 wherein said at least one gradient foam comprises polyurethane, melamine, cellulosic, PVC, polystyrene, polyethylene, or polyester material.

24. The method of claim 20 wherein said at least one gradient foam is formed by a composite of a plurality of gradient foams having different compression ratios.

25. The method of claim 20 wherein said fluid is a liquid having at least one ingredient.

26. The method of claim 20 wherein a viscosity of said fluid is in the range of about 0.1 to about 2000 centipoise.

27. The method of claim 20 wherein said applicator surface area has a domed shape.

28. The method of claim 20 wherein said at least one gradient foam may be chemically modified.

29. The method of claim 20 further comprising the step of:
filling a first gradient foam with a first fluid and filling a second gradient foam with a second fluid wherein said first and second fluids are of a different type and said first and second gradient foams have the same compression ratios.

30. The method of claim 20 further comprising the step of:
filling a first gradient foam with a first fluid and filling a second gradient foam with a second fluid wherein said first and second fluids are of a different type and said first and second gradient foams have different compression ratios.

31. The method of claim 29 or 30 wherein said first and second fluids are applied onto said surface from first and second applicator surface areas, respectively.

32. The method of claim 29 or 30 where said first and second fluids interact to form a third component that is applied onto said surface.

33. The method of claim 29 or 30 wherein said first fluid is deposited onto one side of said surface from a first applicator surface area and said second fluid is deposited onto another side of said surface from a second applicator surface area.

34. The method of claim 20 wherein as the applicator surface area increases, the amount of fluid dispensed onto said surface increases in a directly proportional manner.

35. The method of claim 20 wherein said surface comprises wood, ceramic, plastic, glass, metal, skin, hair, nails, fur, fabric, oral structures or cavities.

36. The method of claim 20 wherein said fluid can be used in application areas comprising home, health/medicine, beauty, feminine, baby, personal, fabric, pet, and food.

* * * * *